United States Patent [19]

Green et al.

[11] Patent Number: 4,932,960
[45] Date of Patent: Jun. 12, 1990

[54] ABSORBABLE SURGICAL FASTENER

[75] Inventors: David T. Green, Westport; Henry Bolanos, East Norwalk; Robert J. Geiste, Milford, all of Conn.

[73] Assignee: United States Surgical Corporation, Norwalk, Conn.

[21] Appl. No.: 401,954

[22] Filed: Sep. 1, 1989

[51] Int. Cl.⁵ ............................................. A61B 17/04
[52] U.S. Cl. .................................................... 606/220
[58] Field of Search .................. 606/220, 219; 227/902

[56] References Cited

U.S. PATENT DOCUMENTS

| D. 280,931 | 10/1985 | Green | D24/26 |
|---|---|---|---|
| D. 280,932 | 10/1985 | Green | D24/26 |
| D. 286,180 | 10/1986 | Korthoff | D24/29 |
| D. 286,441 | 10/1986 | Korthoff | D24/29 |
| D. 286,442 | 10/1986 | Korthoff | D24/27 |
| 4,060,089 | 11/1977 | Noiles | 606/220 |
| 4,402,445 | 9/1983 | Green | 606/220 |
| 4,506,670 | 3/1985 | Crossley | 606/220 |
| 4,513,746 | 4/1985 | Aranyi et al. | 606/220 |
| 4,534,352 | 8/1985 | Korthoff | 606/220 |
| 4,610,250 | 9/1986 | Green | 606/220 |
| 4,667,674 | 5/1987 | Korthoff et al. | 606/220 |
| 4,805,617 | 2/1989 | Bedi et al. | 606/220 |

*Primary Examiner*—Edward M. Coven
*Assistant Examiner*—Gary Jackson
*Attorney, Agent, or Firm*—Thomas R. Bremer; Peter G. Dilworth; Rocco S. Barrese

[57] ABSTRACT

A bioabsorbable surgical fastener comprising a fastener member and an interlocking retainer member. The retainer member has longitudinally extending slots on the lateral sides of the retainer for allowing transverse expansion of the columnar members into which the prongs of the fastener member are locked. Fins on both the lateral and transverse sides of the prongs provide extra strength, and stability during implantation. Stopping surfaces prevent the fastener's barbed tip from exiting the opposite side of the retainer.

11 Claims, 3 Drawing Sheets

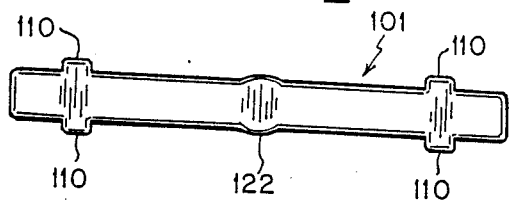
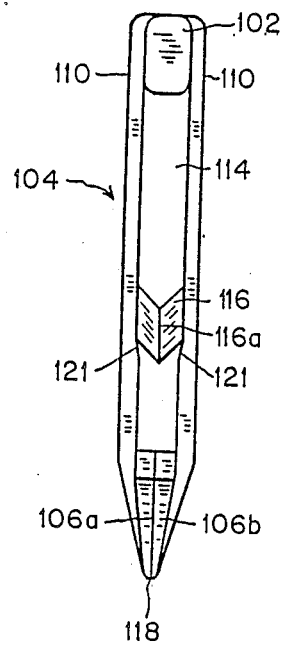
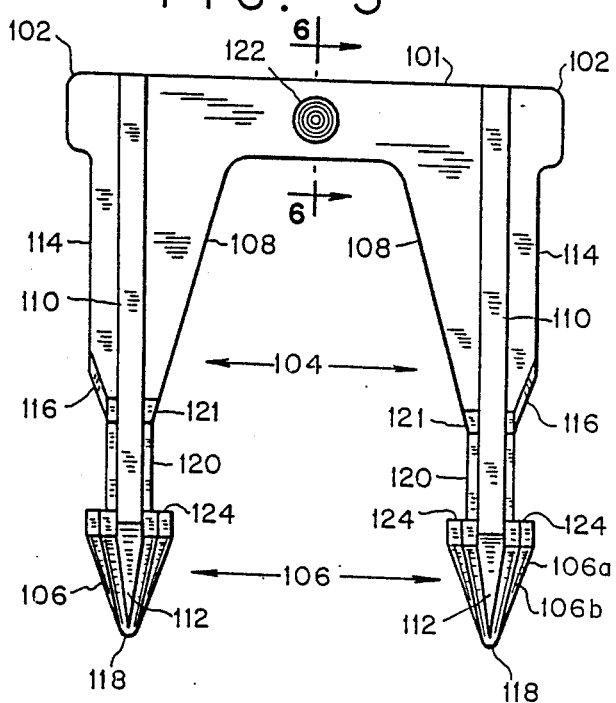
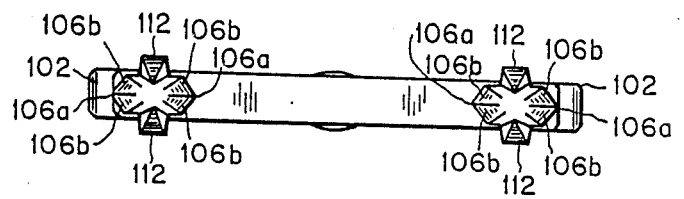
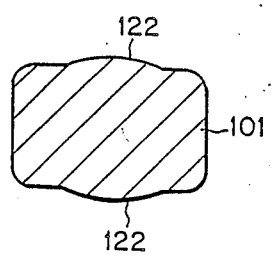

ABSORBABLE SURGICAL FASTENER

BACKGROUND OF THE INVENTION

1. Field of the Invention

This invention relates to surgical fasteners, and more particularly to two part bioabsorbable fasteners comprising a fastener member and retainer piece.

2. Background of Related Art

Surgical fasteners, or staples, are commonly used in surgical procedures to allow a surgeon to fasten body tissue quickly without the need for time-consuming suturing. Such surgical fasteners may be applied by surgical staplers singly, in succession, or a number may be applied simultaneously.

Some types of surgical fasteners are two-part devices. That is, they are composed of a fastener, or staple, portion, which is generally a pronged U-shaped member, and a retainer portion, which has apertures into which the prongs are engaged and held. Such fasteners, once engaged, are not separable. Therefore, once inserted into body tissue they cannot be easily removed. For this reason, two part fasteners are made of bioabsorbable material, such as glycolide, lactide, or copolymers of glycolide and lactide.

One such fastener is disclosed in U.S. Pat. No. 4,060,089 ("Noiles"). A fastener strip with multiple barbed prongs is disclosed, along with a retainer strip with a plurality of longitudinally spaced openings for receiving the prongs.

U.S. Pat. No. 4,402,445 ("Green '445") discloses a two pronged fastener with a retainer piece.

U.S. Pat. No. 4,506,670 ("Crossley") discloses a two part surgical fastener wherein the retainer piece is held to a supporting member by a lug with a frangible member. The prongs of the fastener, upon entering the aperture of the retainer, breaks the frangible member and pushes out the lug, thereby releasing the retainer piece from the supporting member.

U.S. Pat. No. 4,513,746 ("Aranyi et al.") discloses a two piece fastener. The fastener portion has two prongs with outer channels. The retainer piece has extensions with apertures for receiving the prongs of the fastener, and longitudinally extending expansion slots.

U.S. Pat. No. 4,805,617 ("Bedi et al.") discloses a surgical fastener system comprising parallel rows of staples and receivers with the receivers connected to adjacent receivers by a plurality of linkages.

U.S. Pat. No. 4,534,352 ("Korthoff") discloses a surgical fastener member with an increased surface area to volume ratio for faster absorption.

U.S. Pat. No. 4,667,674 ("Korthoff et al.") discloses a surgical fastener having an extended base to reduce hemostatis.

U.S. Pat. No. 4,610,250 ("Green '250") discloses a two part surgical fastener. The fastener member has four prongs which mate with four openings in the retainer member. The two inner prongs are bent toward each other by camming surfaces in the corresponding openings in the retainer.

The following U.S. Design patents also illustrate fasteners: Des. 280,931; Des. 286,441; Des. 286,180; Des. 286,442 and Des. 280,932.

It is often desirable to place multiple rows of fasteners in stitching procedures. Two side by side rows of fasteners aligned end to end along the lengthwise direction of the fastener, for example, will exhibit greater holding power and hemostatis than one such row. To facilitate the placement of multiple rows it is desirable to have a staple which is as narrow as possible. However, the narrower one makes a fastener of any given length and shape, the weaker it is, because there is simply less structural material. For this reason, the structural features of surgical fasteners, which compensate for the lack of material by distributing or reducing stress, become increasingly important as the size is reduced. In particular, stresses are created when the fastener portion is locked into the retainer. This requires expansion of the aperture into which the barbed tip of the fastener prong enters. Although the material of construction, a bioabsorbable resin, has some degree of flexibility and resiliency, the elasticity sometimes can be insufficient to prevent breakage, especially if the retainer member is very narrow. What is needed, then, is a fastener which permits elastic expansion of the retainer piece along the lengthwise direction of the retainer.

SUMMARY OF THE INVENTION

Accordingly, it is one object of the present invention to provide a two part surgical fastener. It is another object of the present invention to provide a bioabsorbable surgical fastener.

It is yet another object of the present invention to provide a surgical fastener which permits elastic expansion of the retainer member.

These and further objects and advantages are achieved herein by providing a surgical fastener comprising:

(a) a fastener member comprising
  (i) a backspan
  (ii) at least two substantially parallel prongs extending substantially perpendicularly from the backspan
  (iii) at least one barb on the distal end of each prong and
(b) a retainer member having
  (i) a base
  (ii) at least two columnar members, each columnar member having an aperture adapted to receive and retain the distal end of a respective one of the prongs, and slot means for allowing expansion of said aperture along the lengthwise direction of the retainer.

BRIEF DESCRIPTION OF THE DRAWINGS

FIG. 2 shows a top view of the fastener portion of the invention;

FIG. 3 shows a side view of the fastener portion of the invention;

FIG. 4 shows a bottom view of the fastener portion of the invention;

FIG. 5 shows an edge view of the fastener portion of the invention;

FIG. 6 illustrates a cross sectional view of the retainer backspan;

DETAILED DESCRIPTION OF THE INVENTION

Two part bioabsorbable fasteners of the type described herein are typically applied by an apparatus such as that described in U.S. Pat. No. 4,655,916 issued to Green, the contents of which are herein incorporated by reference.

The surgical fastener of the present invention generally comprises a unitary plastic like retainer having a longitudinal columnar extension with a longitudinal aperture for receiving the barbed distal end of a fastener prong. The retainer is adapted to be positioned on the distal side of the body tissue to be fastened. The columns each have at least one, and preferably two, longitudinally extending expansion slots on the lateral sides of the column for permitting the column to be transversely expandable about the aperture.

The surgical fastener further comprises a unitary fastener portion initially separate from the retainer and having at least one distally extending prong, the prong being sufficiently rigid to pierce body tissue. The fastener portion is initially positioned on the proximal side of the body tissue to be fastened, and by means of a fastener applying apparatus, is then moved distally through the body tissue and into the aperture in the retainer portion where the barbed distal end of the prongs non-releasably locks into place such the pointed end of the prong does not protrude beyond the bottom of the column.

Figure 1:
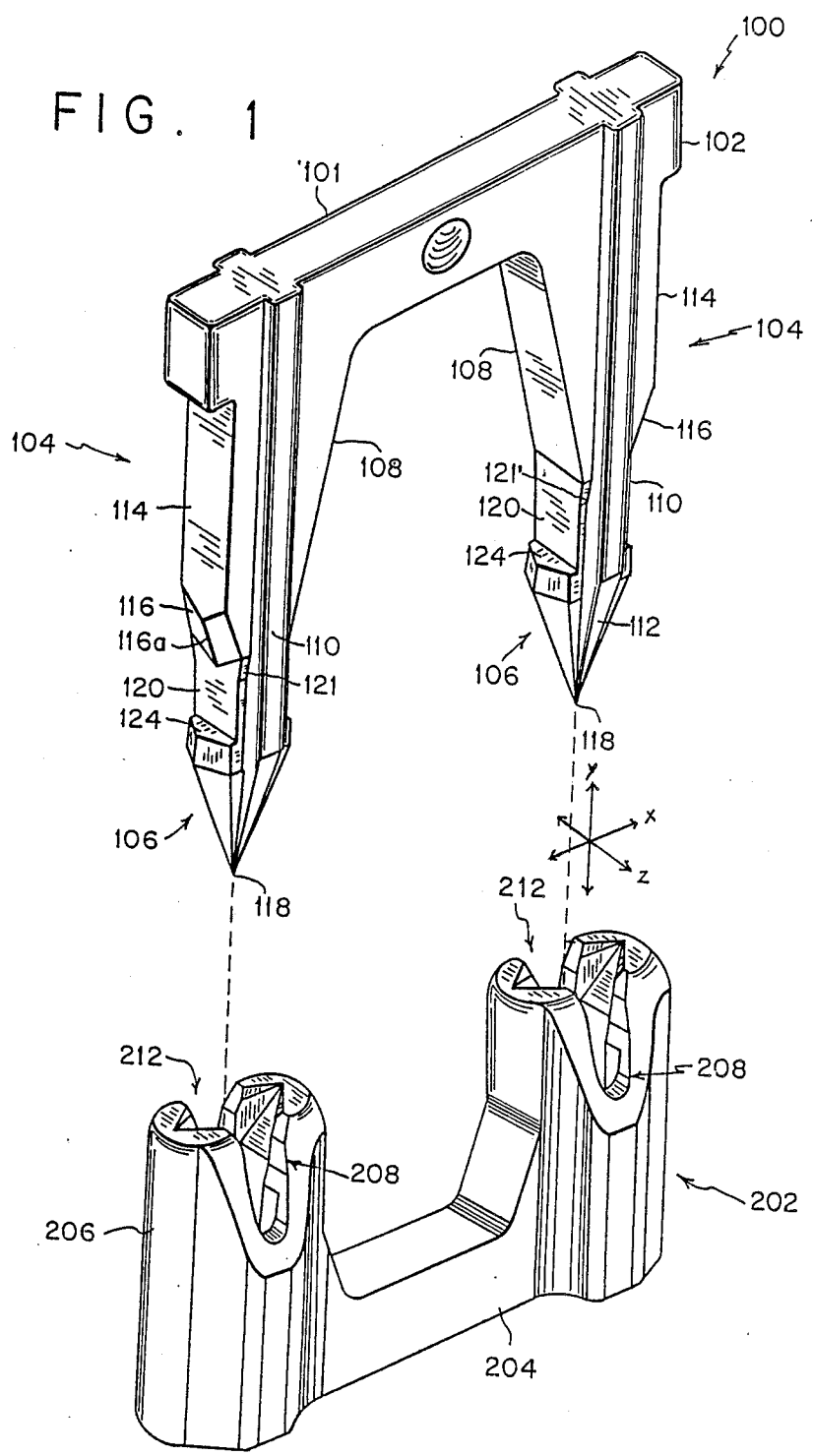
FIG. 1 shows a perspective view of the fastener and retainer.
Figure 7:
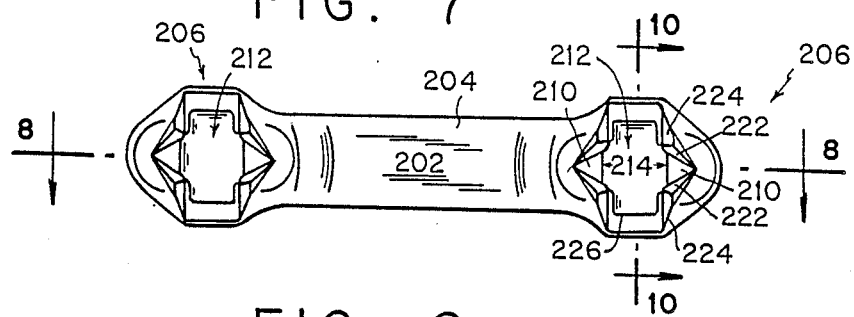
FIG. 7 shows a top view of the retainer.
Figure 8:
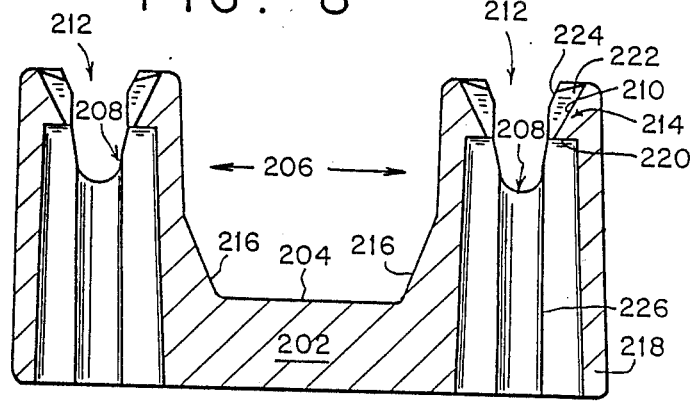
FIG. 8 shows a sectional side view of the retainer.
Figure 9:
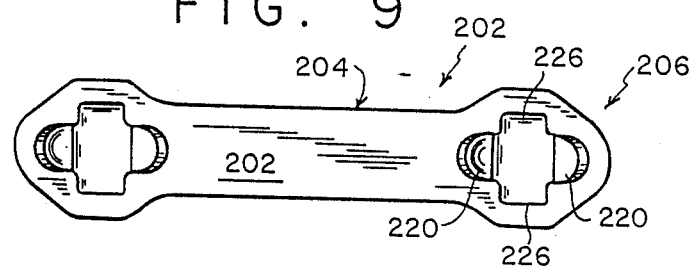
FIG. 9 shows a bottom view of the retainer.
Figure 10:
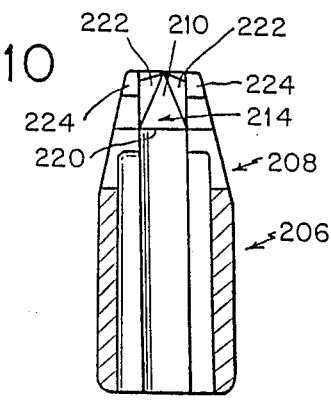
FIG. 10 shows a sectional view of the columnar member of the retainer.

FIG. 1 illustrates a preferred embodiment of the present invention. The U-shaped fastener portion 100 comprises a backspan 101 optionally with transversely projecting extensions 102 to improve hemostasis. Retainer 202 comprises columnar members 206 with apertures 212 and expansion slots 208, and base 204.

Prongs 104 extend substantially perpendicularly from the backspan 101 and are substantially parallel to each other. Prongs 104 each comprise a shank 120 and at least one barb 106 located at the distal end of the prong 104. Barbs 106 each terminate in a distal tip 118 for penetrating body tissue.

With respect to the discussion herein, the "longitudinal" direction, or the direction of the prongs, is the direction illustrated by the arrow Y. The "lateral" or "side by side" direction is the direction illustrated by arrow Z; the transverse direction, which is direction of lengthwise extension of the backspan 101 and base 204, is illustrated by arrow X.

As illustrated in FIGS. 1, 2, 3, 4, 5 and 6, each prong preferably has two barbs 106 projecting from the inner and outer edge respectively of the shank 120 at the distal end of the prong. Alternatively the prongs may have one barb each. The barbs 106 each have a slicing edge 106a for cutting through body tissue, and preferably two wedging surfaces 106b for pushing aside tissue. Each barb 106 also comprises a proximal locking surface 124 which locks into the retainer piece 202 as explained below. Prongs 104 are supported by inside buttress members 108 which give added strength to prevent splaying of the prong as it enters the body tissue to be fastened. Buttress members 108 are substantially triangular shaped integral portions of the fastener which have an inner edge sloping from the backspan 101 to the shank 120.

Lateral fins 110 extend from the top of the backspan 101 to the barbs 106. Sloping surfaces 112 bring the fins 110 to the tips 118 of the barbs 106. Lateral fins 110 reinforce the prongs 104 to resist lateral deflection. Additionally, lateral fins 110 can act as guide rails in conjunction with a fastener applying apparatus to maintain the prongs in perpendicular alignment with the backspan and parallel alignment with each other as the fastener is being inserted into body tissue.

Each fin 114 extends along the outer transverse edge of each prong from the extension 102 of the backspan, to a terminal sloping surface 116 which inclines towards shank 120 in proximity to indentation 121 of said shank 120. The sloping surface 116 ideally possesses an edge 116a to facilitate the penetration of body tissue. In addition to facilitating the passage through body tissue, sloping surface 116 provides a means to lock the fastener 100 in the retainer 202 so that the barbs do not emerge from the opposite end of the apertures 212. This locking feature will be explained in more detail below.

Backspan 101 optionally has a protuberance 122 on each of the two lateral sides, as illustrated in FIGS. 2, 3 and 6. The protuberances perform no function with respect to the tissue fastening operation of the surgical fastener, but provide additional frictional contact with the interior surface of the loading and firing chamber of the fastener implanting instrument to prevent undesirable looseness.

Referring to FIGS. 1, 7, 8, 9 and 10, the retainer portion 202 possesses a base 204, and longitudinal columns 206 with apertures 212 for receiving the prongs 104 of fastener 100. The columns 206 also have longitudinally extending expansion slots 208 to permit transverse expansion of the entrance of aperture 212 in the lengthwise direction of the base 204 when the barb 106 enters the retainer 202.

Column 206 comprises projecting rims 214 having inclined longitudinally aligned camming surfaces 210, inclined guide slopes 222 for the wedging surfaces 106b of the barb 106, inclined guide slopes 224 for the lateral fins 110, and grooves 226 for lateral fins 110. The underside of rim portion 214 comprises a locking surface 220. The column walls 218 are gently inclined so that the aperture diameter widens from the rims to the exit. Columns 206 are braced by buttresses 216 to minimize splaying of the columns 206.

The fastener portion 100 and retainer portion 202 operate in conjunction to form a two piece interlocking surgical fastener. As the distal ends of the prongs 104 enter the respective apertures 212 of the retainer 202, the slicing edges 106a of the barbs 106 come into contact with the respective inclined camming surfaces 210 of the rim 214. Guide slopes 222 and 224 contact the wedging surfaces 106b and the lateral fins 110 respectively, thereby aligning the prongs. As the prongs are pushed into the retainer, the lateral expansion slots 208 allow the mouth of the aperture 212 defined by the opening between the rims 214 to expand transversely to accommodate the barbs 106. After the barbs 106 have passed the rims 214 the opening resiliently returns to its initial position thereby locking the fastener 100 within the retainer 202. Any forces tending to pull the fastener 100 out of the retainer 202 will cause the locking surface 124 of the barb 106 to abut the locking surface 220 of the rim 214. Thus, the fastener, once inserted in the retainer, cannot easily be removed. The terminal sloping surfaces 116 of fins 114 provide a stopping surface to limit the depth to which the prongs are inserted into the fastener. Such limiting of insertion depth confines the barbs 106 entirely within the interior of the column 206 and thereby prevents damage or irritation to body tissue which can be caused by the barb tips 118 protruding beyond the exit opening of the aperture 212. The fastener portion 100 and retainer portion 202 are each integral constructions ideally fabricated from bioabsorbable (or biodegradable) material such as polymers or copolymers of glycolide, lactide, p-dioxanone, polyester, polyamino acids, and the like.

Surgical fasteners of the type described herein may be of any size appropriate to their function of fastening body tissue. For example, the fastener backspan 101 can be about 0.193 inches long including the extensions 102, the prong length including the barb can be about 0.149 inches, the distance between the center line of the prongs 104 can be about 0.141 inches. The retainer 202 can be about 0.201 inches long and about 0.105 inches high (i.e., the height of the columns 206). The angle of the camming surface 210 is optionally about 60° from horizontal, and the angle of the lateral fin guideslopes 224 optimally is about 70° from horizontal. The retainer is about 0.045 inches wide at the widest point. The aperture 212 is about 0.037 inches across in lengthwise distance except at the closest point of the rims 214 which are about 0.018 inches apart.

It should be understood that while the above description contains many specifics, these specifics should not be construed as limitations on the scope of the invention, but merely as exemplifications of preferred embodiments thereof. Those skilled in the art will envision many other possible variations that are within the scope of and spirit of the invention as defined by the claims appended hereto.

What is claimed is:

1. A surgical fastener comprising
   (a) a fastener member comprising
      (i) a backspan
      (ii) at least two substantially parallel prongs extending substantially perpendicularly from said backspan,
      (iii) at least one barb on the distal end of each prong; and
   (b) a retainer member having
      (i) a base
      (ii) at least two columnar members, each columnar member having an aperture adapted to receive and retain the distal end of a respective one of the prongs, and a slot means for allowing expansion of said aperture along the lengthwise direction of the retainer.

2. The surgical fastener of claim 1 wherein said slot means comprises at least one longitudinally extending expansion slot on the lateral side of each columnar member.

3. The surgical fastener of claim 1 additionally comprising a fin extending along the outer transverse edge of each prong.

4. The surgical fastener of claim 1 additionally comprising at least one lateral fin extending along the side of each prong.

5. The surgical fastener of claim 1 wherein said fastener is constructed from a bioabsorbable material.

6. The surgical fastener of claim 5 wherein said bioabsorbable material is selected from the group consisting of polymers of lactide, glycolide, p-dioxanone, polyester and polyaminoacid.

7. The surgical fastener of claim 1 additionally comprising a means to lock the fastener prongs in the retainer member.

8. The surgical fastener of claim 7 wherein said means to lock the fastener prongs into the retainer member comprise a pair of opposing rims in each columnar member, said rims defining the mouth of an aperture for receiving the prongs of the fastener member, said rims being resiliently engagable with the barb of the prong such that the barb is insertable into the aperture of the columnar member, but not removable therefrom.

9. The surgical fastener of claim 8 wherein said rims each comprise a camming surface, said rims being transversely movable in response to pressure exerted on said camming surface from a first position in which the rims do not permit passage of the barbs to a second position permitting passage of the barbs thereby expanding the size of the aperture along the lengthwise direction of the retainer, and said rims being resiliently returnable to the first position when said pressure is removed.

10. The surgical fastener of claim 9 wherein said rims each further comprise a locking surface for retaining the barb within the columnar member.

11. The surgical fastener of claim 1 wherein said backspan includes at least one transversely projecting extension.

* * * * *

UNITED STATES PATENT AND TRADEMARK OFFICE
CERTIFICATE OF CORRECTION

PATENT NO. : 4,932,960
DATED : June 12, 1990
INVENTOR(S) : GREEN et al.

It is certified that error appears in the above—identified patent and that said Letters Patent is hereby corrected as shown below:

In Column 3, line 6 of the patent, change "4,655,916" to --4,665,916--.

Signed and Sealed this

Twenty-third Day of February, 1993

Attest:

STEPHEN G. KUNIN

*Attesting Officer*     Acting Commissioner of Patents and Trademarks